(12) United States Patent
Li et al.

(10) Patent No.: US 6,800,774 B2
(45) Date of Patent: Oct. 5, 2004

(54) CATALYSTS USED FOR OLEFINE POLYMERIZATION AND THE PREPARATION THEREOF

(75) Inventors: Yuesheng Li, Changchun (CN); Jingyu Liu, Changchun (CN); Ke Dai, Changchun (CN); Yi Zheng, Chanchun (CN)

(73) Assignee: Changchun Institute of Applied Chemistry Chinese Academy of Science, Jilin (CN)

( * ) Notice: Subject to any disclaimer, the term of this patent is extended or adjusted under 35 U.S.C. 154(b) by 421 days.

(21) Appl. No.: 09/853,527

(22) Filed: May 10, 2001

(65) Prior Publication Data
US 2002/0082162 A1 Jun. 27, 2002

(30) Foreign Application Priority Data
Dec. 25, 2000 (CN) .......................................... 00136117

(51) Int. Cl.$^7$ ............................ C07F 15/02; C08F 4/06; C08F 110/02; G01J 31/00

(52) U.S. Cl. .......................... 556/33; 556/34; 556/138; 502/159; 502/167; 526/172; 526/352

(58) Field of Search ................................ 502/159, 167; 526/172, 352; 556/33, 34, 138

(56) References Cited

U.S. PATENT DOCUMENTS

| | | | | |
|---|---|---|---|---|
| 3,624,000 A | * | 11/1971 | Throckmorton | 252/429 B |
| 3,668,146 A | * | 6/1972 | Ruhle | 252/428 |
| 6,232,259 B1 | * | 5/2001 | Ittel et al. | 502/155 |

OTHER PUBLICATIONS

US 2002/0082162 A1, US Pre–Grant publication to Li et al., published Jun. 27, 2002, US class 502/167.*

* cited by examiner

*Primary Examiner*—Mark L. Bell
*Assistant Examiner*—J. Pasterczyk
(74) *Attorney, Agent, or Firm*—Dickstein, Shapiro, Morin & Oshinsky, LLP.

(57) ABSTRACT

The present invention provides a polynuclear α-diimine Ni(II) complex used as the precursor of the catalyst in polymerizing polyolefine, represented by the following formula:

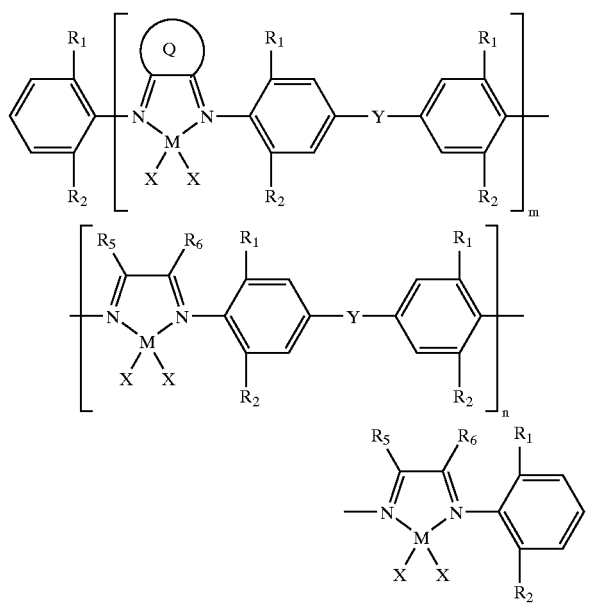

wherein M is Ni; X is Cl or Br; m and n is independently an integer from 0 to 100, respectively; $R_1$ and $R_2$ is the same or different, and is selected from the group consisting of H, methyl, ethyl, isopropyl and tert-butyl; Y is $CR_3R_4$, wherein $R_3$ and $R_4$ is the same or different, and is selected from the group consisting of H, methyl, ethyl, propyl, butyl and phenyl, or $R_3$ and $R_4$ forming a cyclic alkyl group; $R_5$ and $R_6$ is the same or different, and is selected from the group consisting of methyl, ethyl, propyl and heterocyclic group; Q is a cyclic divalent residual group of the following formula or a mixture thereof:

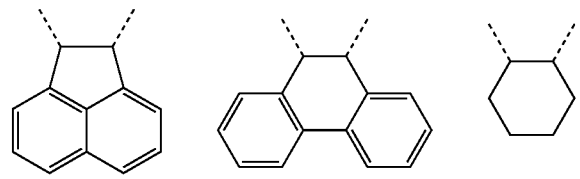

The compound of this invention can be used to catalyze the polymerization of ethylene and to prepare high molecular weight branched polyethylene.

11 Claims, No Drawings

CATALYSTS USED FOR OLEFINE POLYMERIZATION AND THE PREPARATION THEREOF

FIELD OF THE INVENTION

The present invention relates to a catalyst used for olefine polymerization and the preparation thereof. The present invention also relates to a method of polymerizing olefines by using the catalyst of the present invention.

BACKGROUND OF THE INVENTION

Polyolefine is a very important category of polymeric materials. Half of the plastics are polyolefine. They are widely used in industry, agriculture, national defense, communication, transportation and human daily life. Olefines can be polymerized to form macromolecular compounds called polyolefines by using a catalyst. Therefore, catalyst is a key to the development of polyolefine industry which plays a very important role in controlling the structures and properties of polyolefines.

Although the conventional Ziegler-Natta catalysts are still widely used in the industrial production of polyolefines, they are not good catalysts for the manufacture of linear low-density polyethylenes (LLDPE). Recently, it was found that zirconocene, a representative of the metallocene catalysts, possesses very high catalytic activity to copolymerize olefines and can be used for the production of LLDPE. However, an α-olefine (such as butene-1, hexene-1, octene-1, and the like) as the second monomer is required by using metallocene to catalyze the polymerization of olefine for the production of LLDPE, which complicated the process of polymerization. In 1996, Johnson in Du Pont Co. disclosed that α-diimino nickel(II) could be used as an olefine polymerization catalyst (WO 96/23010). With the action of a co-catalyst of methyl aluminoxane (MAO) or modified methyl aluminoxane (MMAO), it is possible to homopolymerize ethylene. By controlling the polymerization conditions, it is possible to obtain polyethylene (PE) including LLDPE with high molecular weight, low density and desired degree of branching.

DISCLOSURE OF THE INVENTION

It is an object of the present invention to provide a catalyst used for olefine polymerization which is a polynuclear α-diimino Ni(II). The precursor of this catalyst is a polynuclear α-diimino Ni(II) complex. The polynuclear α-diimine Ni(II) complex can be activated by a neutral Lewis acids such as MAO, MMAO, which then catalyze the polymerization of ethylene into high molecular weight branched polymeric materials.

The polynuclear α-diimino Ni(II) complex of the present invention has the following structure:

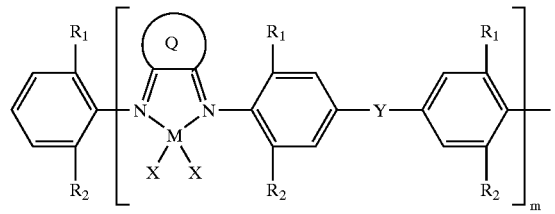

-continued

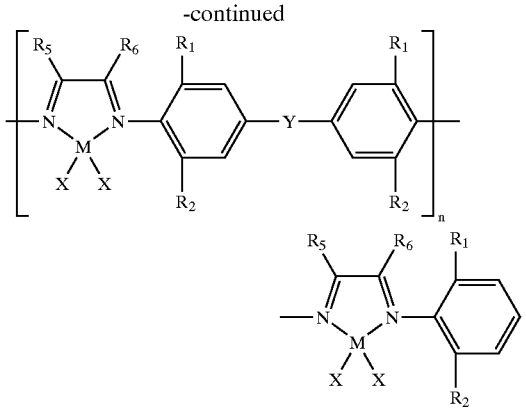

wherein M is Ni; X is Cl or Br, and preferably X is Br; m and n is dependently an integer from 0 to 100, and preferably m is from 1 to 20 and n is from 0 to 30 or m is from 0 to 20 and n is from 1 to 30, more preferably m is from 1 to 10 and n is from 0 to 20 or m is from 0 to 10 and n is from 1 to 20; $R_1$ and $R_2$ may be same or different, and is dependently H, methyl, ethyl, isopropyl or tert-butyl, preferably $R_1$ is isopropyl and $R_2$ is methyl or isopropyl; Y is $CR_3R_4$, wherein $R_3$ and $R_4$ may be same or different, and is dependently H, methyl, ethyl, propyl, butyl or phenyl, preferably $R_3$ and $R_4$ are the same, and are H or methyl, or $R_3$ and $R_4$ forming a cyclohexyl group; $R_5$ and $R_6$ may be same or different, and is dependently methyl, ethyl or heterocyclic group (such as 2-pyridyl group), preferably $R_5$ and $R_6$ are the same, and are methyl; Q is a divalent residual represent by the following formula or a mixture thereof:

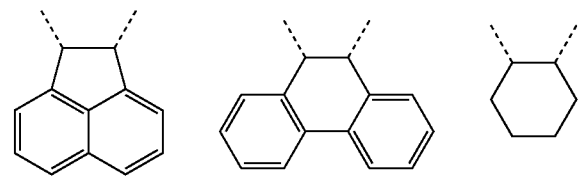

preferably Q is a divalent residual of the following formula:

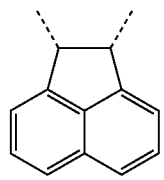

The polynuclear α-diimino Ni(II) complex of the present invention can be prepared by a method comprising the following steps:

(a) condensing an α-diketone represented by the formula or a mixture thereof,

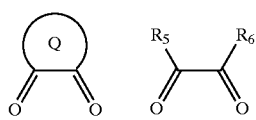

wherein, Q, $R_5$ and $R_6$ are as defined above, a substituted aromatic diamine represented by the formula

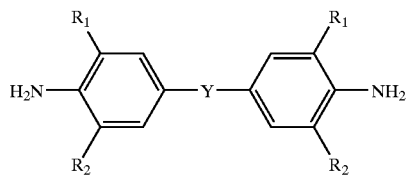

wherein, $R_1$, $R_2$ and Y are as defined above,
and a substituted aromatic amine represented by the formula

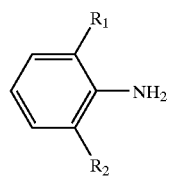

wherein, $R_1$ and $R_2$ are as defined above, in a medium of alcohol, aromatic hydrocarbon, alcohol-ether mixture, or alcohol-halogenated hydrocarbon mixture and under the catalytic action of HCOOH, $CF_3COOH$ or HX, wherein X is F, Cl, Br, or I;
thereby obtaining an oligomer of substituted α-diimine of the formula

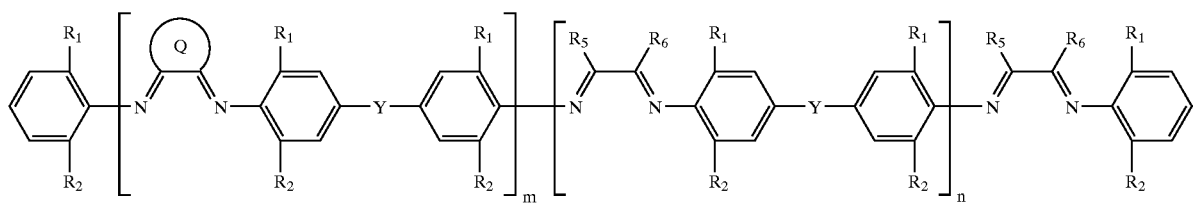

wherein, $R_1$, $R_2$, $R_5$, $R_6$, Q, Y, m and n have the same definition of above;

(b) carrying out coordination reaction of the oligomer of step (a) with $NiX_2$, wherein X is Cl or Br, in the absence of water and oxygen, thereby obtaining a polynuclear α-diimino Ni(II) complex of the following formula:

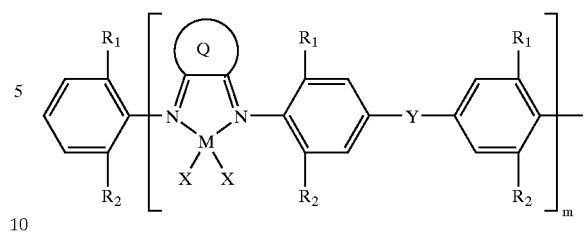

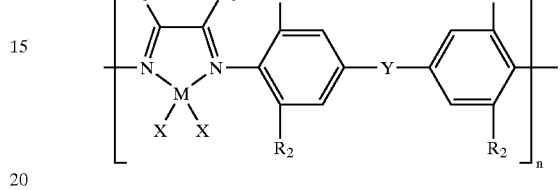

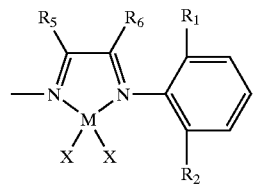

wherein, $R_1$, $R_2$, $R_5$, $R_6$, Q, Y, M, X, m and n have the same definition of above.

The reaction process can be represent by the following scheme:

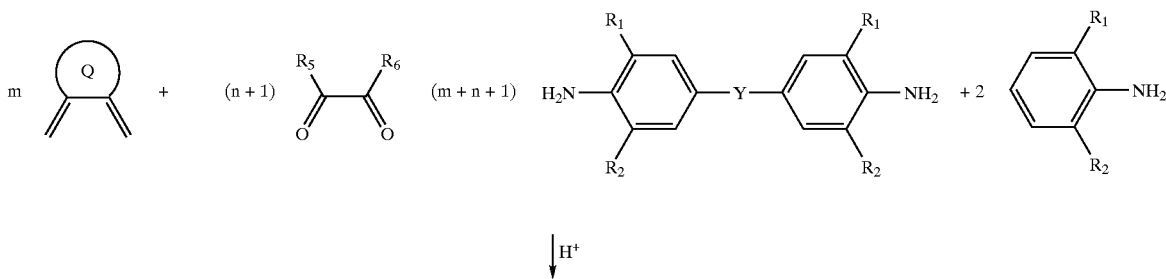

-continued

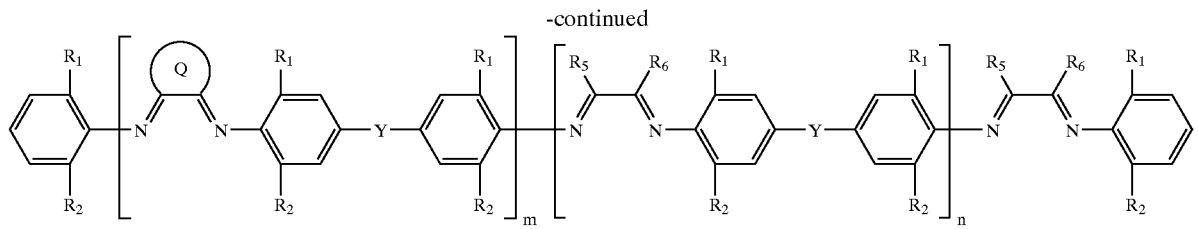

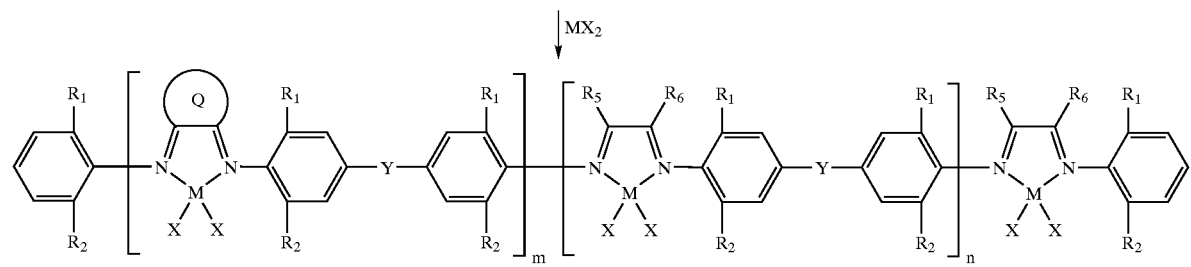

wherein, $R_1$, $R_2$, $R_5$, $R_6$, Q, Y, M, X, m and n have the same definition of above.

The polynuclear α-diimino Ni(II) complex of the present invention is capable of catalyzing the polymerization of ethylene under the action of neutral Lewis acid such as MAO or MMAO and the like. Thus, polyethylene with high molecular weight can be obtained.

EXAMPLES

Example 1

To a 150 ml reaction flask, 1.457 g (8.0 mmol) of acenaphthenedione, 1.405 g (4.0 mmol) of di(4-amino-3-chloro-5-isopropylphenyl)methane, and 50 ml ethanol were added, stirred and dissolved. Then, 1.0 ml HCOOH was added dropwise and the mixture was refluxed for 24 hours. After cooling, 1.507 g (8.5 mmol) of 2,6-diisopropyl aniline was added and the mixture was heated, refluxed for 24 hours. After cooling, the mixture was poured into 200 ml of petroleum ether under stirring and filtered. The filter cake was washed twice with cold methanol and dried in vacuum at 60° C. for 48 hours. 3.37 g of dimer of α-diimine (yield 84.4%) was obtained.

Example 2

To a 150 ml reaction flask, 1.093 g (6.0 mmol) of acenaphthenedione, 1.579 g (4.0 mmol) of 2,2-di(4-amino-3,5-diisopropyl phenyl) propane, and 50 ml ethanol were added, stirred and dissolved. Then 1.0 ml trifluoroacetic acid was added dropwise and the mixture was refluxed for 24 hours. After cooling, 0.762 g (4.3 mmol) of 2,6diisopropyl aniline was added. The following procedure was the same as Example 1. 2.78 g of trimer of α-diimine (yield 87.9%) was obtained.

Example 3

To a 150 ml reaction flask, 1.093 g (6.0 mmol) of acenaphthenedione, 2.055 g (4.5 mmol) of 1,1'-di(4-amino-3,5-diisopropylphenyl) phenylethane, and 50 ml toluene were added, stirred and dissolved. Then three drops of HCl were added, and the mixture was refluxed for 8 hours. After cooling, 0.585 g (3.3 mmol) of 2,6-diisopropyl aniline was added and the mixture was heated, and refluxed for 12 hours. After cooling and placing overnight, the reactant was filtered. The filter cake was washed twice with cold methanol and dried in vacuum at 60° C. for 48 hours. 3.17 g of oligomer of α-diimine (yield 91.5%) was obtained.

Example 4

To a 150 ml dried reaction flask, 1.366 g (7.5 mmol) of acenaphthenedione, 2.11 5 g (6.0 mmol) of 2,2-di(4-amino-3-methyl-5-isopropylphenyl) butane, and 50 ml ethanol were added, stirred and dissolved. 1.0 ml of HCOOH was added dropwise, and the mixture was refluxed for 24 hours. After cooling, 0.478 g (3.2 mmol) of 2-methyl-6-isopropyl aniline was added, and the mixture was heated and refluxed for 24 hours. The rest of the procedure was the same as in Example 1. 3.38 g of oligomer of α-diimine (yield 92.3%) was obtained.

Example 5

To a 150 ml dried reaction flask, 1.275 g (7.0 mmol) of acenaphthenedione, 2.608 g (6.0 mmol) of 1,1-di(4-amino-3,5-diisopropylphenyl) cyclohexane, and 50 ml ethanol were added, stirred and dissolved. Then, 1.0 ml HCOOH was added and the mixture was refluxed for 24 hours. After cooling, 0.390 g (2.2 mmol) of 2,6-diisopropyl aniline and 10 ml chloroform was added, and the mixture was heated and refluxed for 24 hours. The rest of the procedure was the same as in Example 1. 3.67 g of oligomer of α-diimine (yield 92.1 %) was obtained.

Example 6

To a 150 ml dried reaction flask, 0.984 g (5.4 mmol) of acenaphthenedione, 0.186 g (0.6 mmol) of di(4-amino-3,5-diethylphenyl) methane, 1.826 g (4.2 mmol) of 1,1-di(4-amino-3,5-diisopropylphenyl) cyclohexane, and 40 ml ethanol were added, stirred and dissolved. Then 1.0 ml HCOOH was added dropwise and the mixture was refluxed for 24 hours. After cooling, 0.248 g (1.4 mmol) of 2,6-diisopropyl aniline and 10 ml tetrahydrofuran were added, and the mixture was heated and refluxed for 24 hours. The rest of the procedure was the same as in Example 1. 3.07 g of oligomer of α-diimine (yield 93.7 %) was obtained.

Example 7

The process of Example 6 was carried out, except that 0.169 g (0.6 mmol) of 2,2-di(4-amino-3,5-dimethylphenyl) propane was used in place of Di(4-amino-3,5-diethylphenyl) methane in Example 6. 3.02 g of dimer of α-diimine (yield 92.7%) was obtained.

Example 8

The process of Example 6 was carried out, except that 0.186 g (0.6 mmol) of di(4-amino-3-tert-butylphenyl) methane was used in place of Di(4-amino-3,5-diethylphenyl) methane in Example 6. 3.00 g of dimer of α-diimine (yield 91.6%) was obtained.

Example 9

To a 150 ml reaction flask, 1.664 g (8.0 mmol) of phenanthrenequinone, 1.354 g (4.0 mmol) of 2,2di(4-amino-3-methyl-5-isopropylphenyl)propane, and 50 ml ethanol were added, stirred and dissolved. Then, 1.0 ml trifluoroacetic acid was added dropwise and the mixture was refluxed for 3 days. After cooling, 1.269 g (8.5 mmol) of 2-methyl-6-isopropyl aniline was added, and the mixture was heated and refluxed for 24 hours. After cooling and placing overnight, the reactant was filtered. The filter cake was washed twice with cold methanol and vacuum dried at 60° C. for 48 hours. 3.36 g of oligomer of α-diimine (yield 85.6%) was obtained.

Example 10

To a 150 ml reaction flask, 0.897g (8.0 mmol) of 1,2-cyclohexanedione, 1.466 g (4.0 mmol) of di(4-amino3,5-diisopropyl phenyl)methane, and 50 ml ethanol were added, stirred and dissolved. Then 1.0 ml of formic acid was added dropwise and the mixture was refluxed for 5 days. After cooling, 1.596 g (9.0 mmol) of 3,5-diisopropyl aniline was added, and the mixture was heated and refluxed for 7 days. After cooling, the mixture was concentrated and eluted by column (petroleum ether/ethyl acetate mixed solvent as eluant). 1.72 g of product was obtained (yield 49.2%).

Example 11

To a 150 ml reaction flask, 1.698 g (8.0 mmol) of 2,2-di-pyridyl ethanedione, 1.466 g (4.0 mmol) of di(4-amino-3,5-diisopropylphenyl) methane, 50 ml of toluene and 3 drops of HCl were added, and the mixture was refluxed for 4 days. After cooling, 1.773 g (10.0 mmol) of 3,5-diisopropyl aniline was added and the mixture was heated and refluxed for 7 days. Then the mixture were cooled, concentrated and eluted by column (petroleum ether/ethyl acetate mixed solvent as eluant), and 1.49 g of product was obtained (yield 34.8%).

Example 12

To a 150 ml reaction flask, 0.620 g (7.2 mmol) of 2,3-butanedione, 2.346 g (6.4 mmol) of di(4-amino-3,5-diisopropyl phenyl) methane, and 50 ml of ethanol were added and stirred. Then, 1.0 ml of formic acid was added dropwise, and the mixture was heated and refluxed for 24 hours. After cooling, 0.319 g (1.8 mmol) of 2,6-diisopropyl aniline was added and the mixture was heated and refluxed for 24 hours. After cooling, The mixture was poured into 200 ml petroleum ether while stirring and then filtered. The filter cake was washed twice with methanol and vacuum dried at 60° C. for 48 hours. 2.68 g of oligomer of α-diimine (yield 89.3%) was obtained.

Example 13

To a 150 ml reaction flask, 0.560 g (6.5mmol) of 2,3-butanedione, 2.199 g (6.0 mmol) of di(4-amino-3,5-diisopropyl phenyl) methane, and 50 ml of ethanol were added and stirred. Then, 1.0 ml of formic acid was added dropwise, and the mixture was heated and refluxed for 24 hours. After cooling, 0.212 g (1.2 mmol) of 2,6-diisopropyl aniline was added. The rest of the procedure was the same as in Example 12. 2.51 g of oligomer of α-diimine (yield 92.9%) was obtained.

Example 14

To a 150 ml reaction flask, 0.585 g (6.8 mmol) of 2,3-butanedione, 2.346 g (6.4 mmol) of di(4-amino-3,5-diisopropylphenyl) methane, and 50 ml of ethanol were added and stirred. Then, 1.0 of ml formic acid was added dropwise, and the mixture was heated and refluxed for 24 hours. After cooling, 0.177 g (1.0 mmol) of 2,6-diisopropyl aniline was added. The rest of the procedure was the same as in Example 12. 2.69 g of oligomer of α-diimine (yield 95.1 %) was obtained.

Example 15

To a 150 ml reaction flask, 0.631 g (6.3 mmol) of 2,3-butanedione, 2.200 g (6.0 mmol) of di(4-amino-3,5-diisopropylphenyl) methane, and 50 ml of ethanol were added and stirred. Then, 1.0 ml formic acid was added dropwise, and the mixture was heated and refluxed for 24 hours. After cooling, 0.142 g (0.8mmol) of 2,6-diisopropyl aniline was added. The rest of the procedure was the same as in Example 12. 2.60 g of oligomer of α-diimine (yield 96.0%) was obtained.

Example 16

To a dried 150 ml reaction flask, 1.093 g (6.0 mmol) of acenaphthanedione, 0.312 g (1.5 mmol) of phenanthrenequinone, 2.368 g (6.0 mmol) of 2,2-di(4-amino-3,5-diisopropylphenyl)propane, and 50 ml of ethanol were added, stirred and dissolved. Then, 1.0 ml of formic acid was added dropwise, and the mixture was heated and refluxed for 24 hours. After cooling, 0.567 g (3.2 mmol) of 2,6-diisopropyl aniline was added, and the mixture was heated and refluxed for 24 hours. The rest of the procedure was the same as in Example 1. 3.78g of oligomer of α-diimine (yield 93.7%) was obtained.

Example 17

To a dried 150 ml reaction flask, 0.601 g (3.3 mmol) of acenaphthanedione, 0.284 g (3.3 mol) of 2,3-butanedione, 2.199 g (6.0 mmol) of 2,2-di(4-amino-3,5-diisopropyl phenyl) methane, and 50 ml ethanol were added, stirred and dissolved. Then, 1.0 ml of formic acid was added and the mixture was refluxed for 24 hours. After cooling, 0.283 g (1.6 mmol) of 2,6-diisopropyl aniline was added, and the mixture was heated and refluxed for 24 hours. The rest of the procedure was the same as in Example 1. 2.88g of oligomer of α-diimine (yield 94.1%) was obtained.

Example 18

To a dried 150 ml reaction flask, 0.219 g (1.2 mmol) of phenanthrenedione, 0.465 g (5.4 mmol) of 2,3-butanedione, 2.199 g (6.0 mmol) of 2,2-di(4-amino-3,5-diisopropylphenyl)methane, and 50 ml of ethanol were added, stirred and dissolved. Then, 1.0 ml of formic acid was added dropwise and the mixture was refluxed for 24 hours. After cooling, 0.283 g (1.6 mmol) of 2,6-diisopropyl aniline was added and the mixture was heated and refluxed for 24 hours. The rest of the procedure was the same as in Example 1. 2.70 g of oligomer of α-diimine (yield 93.4%) was obtained.

Example 19

Under argon atmosphere, to a dried 100 ml Schlenk flask, 0.437 g (2.0 mmol) of NiBr$_2$, 10 ml anhydrous CH$_2$Cl$_2$, and 0.19 g of glycol dimethyl ether were added. The mixture was stirred for 15 minutes and then 0.998 g of α-diimine dimer prepared in Example 1 and 10 ml anhydrous CH$_2$Cl$_2$ were added, and the mixture was refluxed for 24 hours. After cooling, the mixture was poured into 60 ml of ethanol/petroleum ether mixture and filtered. The filter cake was washed 3 times with a little ether and vacuum dried at 60° C. for 24 hours. 1.200 g (yield 83.6%) of dimer of α-diimino nickel(II) bromide was obtained.

Example 20

The process of Example 19 was carried out, except that 1.055 g of trimer of α-diimine prepared in Example 2 was used in place of the dimer of α-diimine prepared in Example 1. 1.253 g (yield 84%) of trimer of α-diimino nickel(II) bromide was obtained.

Example 21

The process of Example 19 was carried out, except that 1.151 g of oligomer of a diimine prepared in Example 3 was used in place of the dimer of a diimine prepared in Example 1. 1.296 g (yield 81.6%) of oligomer of α-diimino nickel(II) bromide was obtained.

Example 22

The process of Example 19 was carried out, except that 0.976 g of oligomer of α-diimine prepared in Example 4 was used in place of the dimer of α-diimine prepared in Example 1. 1.19 g (yield 84.2%) of oligomer of α-diimino nickel(II) bromide was obtained.

Example 23

The process of Example 19 was carried out, except that 1.139 g of oligomer of α-diimine prepared in Example 5 was used in place of the dimer of α-diimine prepared in Example 1. 1.344 g (yield 85.3%) of oligomer of α-diimino nickel(II) bromide was obtained.

Example 24

The process of Example 19 was carried out, except that 1.213 g of oligomer of α-diimine prepared in Example 6 was used in place of the dimer of α-diimine prepared in Example 1. 1.439 g (yield 87.2%) of oligomer of α-diimino nickel(II) bromide was obtained.

Example 25

Under argon atmosphere, to a dried 100 ml Schlenk flask, 0.259 g (2.0 mmol) of $NiCl_2$, 10 ml anhydrous $CH_2Cl_2$ and 0.19 g of glycol dimethyl ether were added. The mixture was stirred for 15 minutes, then 1.213 g of α-diimine oligomer prepared in Example 7 and 10 ml of anhydrous $CH_2Cl_2$ were added, and thereafter, the mixture was refluxed for 24 hours. The rest of the procedure was the same as in Example 19. 1.257 g (yield 85.4) of oligomer of α-diimino nickel(II) chloride was obtained.

Example 26

The process of Example 19 was carried out, except that 1.213 g of oligomer of α-diimine prepared in Example 8 was used in place of the dimer of α-diimine prepared in Example 1. 1.481 g (yield 89.7%) of oligomer of α-diimino nickel(II) bromide was obtained.

Example 27

The process of Example 19 was carried out, except that 0.981 g of oligomer of α-diimine prepared in Example 9 was used in place of the dimer of α-diimine prepared in Example 1. 1.191 g (yield 84.0%) of oligomer of α-diimino nickel(II) bromide was obtained.

Example 28

The process of Example 19 was carried out, except that 0.873 g of the product prepared in Example 10 was used in place of the dimer of α-diimine prepared in Example 1. 1.081 g (yield 82.5%) of dimer of α-diimino nickel(II) bromide was obtained.

Example 29

The process of Example 19 was carried out, except that 1.070 g of dimer of α-diimine prepared in Example 11 was used in place of the dimer of α-diimine prepared in Example 1. 1.252 g (yield 83.1%) of oligomer of a diimino nickel(II) bromide was obtained.

Example 30

The process of Example 19 was carried out, except that 0.831 g of oligomer of α-diimine prepared in Example 12 was used in place of the dimer of α-diimine prepared in Example 1. 1.047 g (yield 82.6%) of oligomer of α-diimino nickel(II) bromide was obtained.

Example 31

The process of Example 19 was carried out, except that 0.831 g of oligomer of α-diimine prepared in Example 13 was used in place of the dimer of α-diimine prepared in Example 1. 1.066 g (yield 84.1%) of oligomer of α-diimino nickel(II) bromide was obtained.

Example 32

The process of Example 19 was carried out, except that 0.832 g of oligomer of α-diimine prepared in Example 14 was used instead of the dimer of α-diimine prepared in Example 1. 1.091 g (yield 86.0%) of oligomer of α-diimino nickel(II) bromide was obtained.

Example 33

The process of Example 19 was carried out, except that 0.860 g of oligomer of α-diimine prepared in Example 15 was used in place of the dimer of α-diimine prepared in Example 1. 1.148 g (yield 88.5%) of oligomer of α-diimino nickel(II) bromide was obtained.

Example 34

The process of Example 19 was carried out, except that 1.345 g of oligomer of α diimine prepared in Example 16 was used in place of the dimer of α-diimine prepared in Example 1. 1.622 g (yield 91.0%) of oligomer of α-diimino nickel(II) bromide was obtained.

Example 35

The process of Example 19 was carried out, except that 1.020 g of oligomer of α-diimine prepared in Example 17 was used in place of the dimer of α-diimine prepared in Example 1. 1.370 g (yield 94.1%) of oligomer of α-diimino nickel(II) bromide was obtained.

Example 36

The process of Example 19 was carried out, except that 0.963 g of oligomer of α-diimine prepared in Example 18 was used in place of the dimer of α-diimine prepared in Example 1. 1.289 g (yield 92.1%) of oligomer of α-diimino nickel(II) bromide was obtained.

Example 37

Under ethylene atmosphere, to a dried 250 ml flask, 14.4 mg (20 μmmol Ni) of dimer of α-diimino nickel bromide prepared in Example 19 and 50 ml of absolute toluene were added. The dimer was dissolved with stirring and the mixture was heated to 35° C. 8 ml of 1M MAO was added, and the polymerization reaction was allowed to proceed under normal pressure for 30 minutes. The mixture was poured into 200 ml of 1% ethanol solution of HCl/water (2:1). The toluene layer was separated, and toluene was evaporated by reduced pressure. 0.58 g of a rubbery polymer was obtained. The catalytic efficiency is $5.8 \times 10^4$ g PE/mol Ni·h.

Example 38

The process of Example 37 was carried out, except that 25 mg (20 μmol Ni)of trimer of α-diimine Ni(II) bromide prepared in Example 20 was used in place of the dimer of α-diimino nickel bromide prepared in Example 19. 0.54 g of a rubbery polymer was obtained. The catalytic efficiency is $5.4 \times 10^4$ g PE/mol Ni·h.

Example 39

The process of Example 37 was carried out, except that 23.8 mg (30 μmol Ni) of the oligomer of α-diimino nickel bromide prepared in Example 21 was used in place of the dimer of α-diimino nickel bromide prepared in Example 19. 0.79 g of a rubbery polymer was obtained. The catalytic efficiency is $5.3 \times 10^4$ g PE/mol Ni·h.

Example 40

The process of Example 37 was carried out, except that 18.4 mg (26 μmol Ni) of the oligomer of α-diimino nickel bromide prepared in Example 22 was used in place of the dimer of α-diimino nickel bromide prepared in Example 19. 0.64 g of a rubbery polymer was obtained. The catalytic efficiency is $4.8 \times 10^4$ g PE/mol Ni·h.

Example 41

The process of Example 37 was carried out, except that 16.6 mg (21 μmol Ni) of the oligomer of α-diimino nickel bromide prepared in Example 23 was used in place of the dimer of α-diimino nickel bromide prepared in Example 19. 0.56 g of a rubbery polymer was obtained. The catalytic efficiency is $5.3 \times 10^4$ g PE/mol Ni·h.

Example 42

The process of Example 37 was carried out, except that 16.5 mg (20 μmol Ni) of the oligomer of α-diimino nickel bromide prepared in Example 24 was used in place of the dimer of α-diimino nickel bromide prepared in Example 19. 0.51 g of a rubbery polymer was obtained. The catalytic efficiency is $5.1 \times 10^4$ g PE/mol Ni·h.

Example 43

The process of Example 37 was carried out, except that 19 mg (23 μmol Ni) of the oligomer of α-diimino nickel chloride prepared in Example 25 was used in place of the dimer of α-diimino nickel bromide prepared in Example 19. 0.53 g of a rubbery polymer was obtained. The catalytic efficiency is $4.6 \times 10^4$ g PE/mol Ni·h.

Example 44

The process of Example 37 was carried out, except that 19.8 mg (24 μmol Ni) of the oligomer of α-diimino nickel bromide prepared in Example 26 was used in place of the dimer of α-diimino nickel bromide prepared in Example 19. 0.59 g of a rubbery polymer was obtained. The catalytic efficiency is $4.9 \times 10^4$ g PE/mol Ni·h.

Example 45

The process of Example 37 was carried out, except that 14.2 mg (20 μmol Ni) of the dimer of α-diimino nickel bromide prepared in Example 27 was used in place of the dimer of α-diimino nickel bromide prepared in Example 19. 0.42 g of a rubbery polymer was obtained. The catalytic efficiency is $4.2 \times 10^4$ g PE/mol Ni·h.

Example 46

The process of Example 37 was carried out, except that 16.8 mg (25.8 11 μmol Ni) of the dimer of α-diimino nickel bromide prepared in Example 28 was used in place of the dimer of α-diimino nickel bromide prepared in Example 19. 0.82 g of a rubbery polymer was obtained. The catalytic efficiency is $6.4 \times 10$ g PE/mol Ni·h.

Example 47

The process of Example 37 was carried out, except that 15.1 mg (20 μmol Ni) of the dimer of α-diimino nickel bromide prepared in Example 29 was used in place of the dimer of α-diimino nickel bromide prepared in Example 38. 0.38 g of a rubbery polymer was obtained. The catalytic efficiency is $3.8 \times 10^4$ g PE/mol Ni·h.

Example 48

Under ethylene atmosphere, to a dried 250 ml reaction flask, 15 mg (23.6 μmol Ni) of the oligomer of α-diimino nickel bromide prepared in Example 30 and 50 ml of absolute toluene were added, and the mixture was stirred and dissolved. The solution was heated to 35° C. Then, 9 ml of 1M MAO was added, and the polymerization reaction was allowed to proceed under normal pressure for 60 minutes. Then, the mixture was poured into 200 ml of 1% ethanol solution of HCl, filtered and washed 3 times with ethanol and finally vacuum dried at room temperature. 0.35 g of a polymer was obtained. The catalytic efficiency is $1.5 \times 10^4$ g PE/mol Ni·h.

Example 49

The process of Example 48 was carried out, except that 18 mg (28.4 P mol Ni) of the oligomer of α-diimino nickel bromide prepared in Example 31 was used in place of the oligomer of α-diimino nickel bromide prepared in Example 30. 0.40 g of a polymer was obtained. The catalytic efficiency is $1.4 \times 10^4$ g PE/mol Ni·h.

Example 50

The process of Example 48 was carried out, except that 20 mg (31.5 μmol Ni) of the oligomer of α-diimino nickel bromide prepared in Example 32 was used in place of the oligomer of α-diimino nickel bromide prepared in Example 30. 0.51 g of a polymer was obtained. The catalytic efficiency is $1.6 \times 10^4$ g PE/mol Ni·h.

Example 51

The process of Example 48 was carried out, except that 21 mg (32.5 μmol Ni) of the oligomer of α-diimino nickel bromide prepared in Example 33 was used in place of the oligomer of α-diimino nickel bromide prepared in Example 30. 0.48 g of a polymer was obtained. The catalytic efficiency is $1.5 \times 10^4$ g PE/mol Ni·h.

Example 52

The process of Example 37 was carried out, except that 20.3 mg (22.9 μmol Ni) of the oligomer of α-diimino nickel bromide prepared in Example 34 was used in place of the dimer of α-diimino nickel bromide prepared in Example 19. 0.62 g of a rubbery polymer was obtained. The catalytic efficiency is $5.4 \times 10^4$ g PE/mol Ni·h.

Example 53

The process of Example 37 was carried out, except that 20mg (22.5 μmol Ni) of the oligomer of α-diimino nickel bromide prepared in Example 35 was used in place of the dimer of α-diimino nickel bromide prepared in Example 19. 0.44 g of a rubbery polymer was obtained. The catalytic efficiency is $3.3 \times 10^4$ g PE/mol Ni·h.

Example 54

The process of Example 37 was carried out, except that 15 mg (21.5 μmol Ni) of the oligomer of α-diimino nickel bromide prepared in Example 36 was used in place of the dimer of α-diimino nickel bromide prepared in Example 19. 0.44 g of a rubbery polymer was obtained. The catalytic efficiency is $2 \times 10^4$ g PE/mol Ni·h.

Example 55

Under ethylene atmosphere, to a dried 1 liter autoclave, 75 mg (0.1 μmmol Ni) of the trimer of α-diimino nickel bromide prepared in Example 20 and 300 ml absolute toluene were added. The trimer was dissolved with stirring and the mixture was heated to 35° C. 50 ml of 1M MAO was added, and the pressure was raised. The polymerization reaction was allowed to proceed under 1.0 MPa for 30 minutes. The polymerization reaction was terminated with 1% ethanol solution of HCl. The reaction mixture was filtered and vacuum dried at 60° C. for 24 hours. 104 g of a polymer was obtained. The catalytic efficiency is $2.1 \times 10^6$ g PE/mol Ni·h.

We claim:

1. A polynuclear α-diimine Ni(II) complex represented by the following formula:

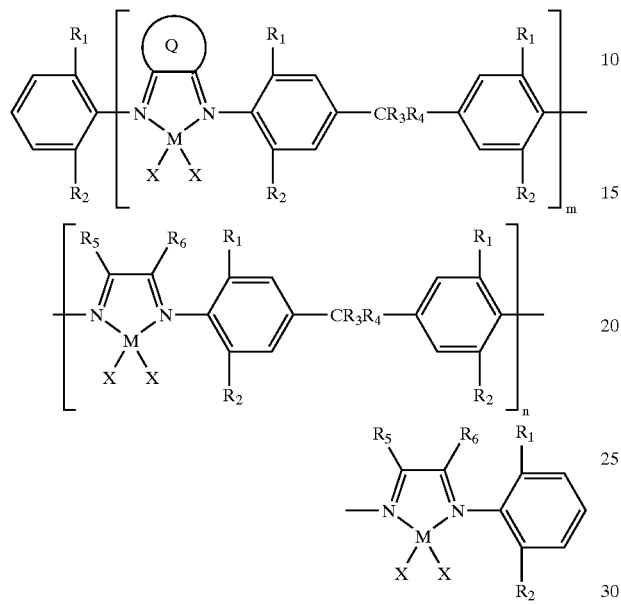

wherein M is Ni; X is Cl or Br; m is an integer from 0 to 100, and n is an integer from 0 to 100; wherein at least one of m and n is not 0; $R_1$ and $R_2$ are the same or different, and are selected from the group consisting of H, methyl, ethyl, isoprpyl and tert-butyl; wherein $R_3$ and $R_4$ are the same or different, and are selected from the group consisting of H, methyl, ethyl, propyl, butyl and phenyl, or $R_3$ and $R_4$ form a cyclic alkyl group; $R_5$ and $R_6$ are the same or different, and are selected from the group consisting of methyl, ethyl, propyl and a heterocyclic group; and each Q is independently;

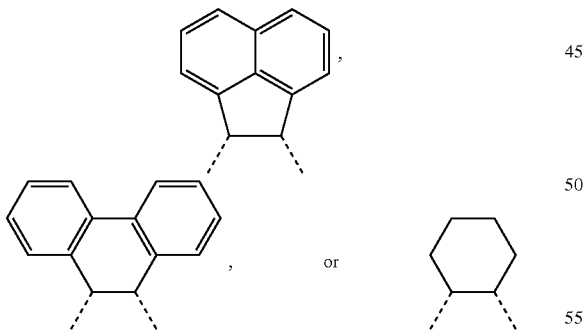

2. A polynuclear α-diimine Ni(II) complex of claim 1, wherein m is an integer from 1 to 100 and n is 0.

3. A polynuclear α-diimine Ni(II) complex of claim 1, wherein, X is Br; m is an integer from 1 to 20, n is 0; $R_1$ is isopropyl, $R_2$ is methyl or isopropyl; and $R_3$ and $R_4$ are the same and are H or methyl, or $R_3$ and $R_4$ form a cyclohexyl group.

4. A polynuclear α-diimine Ni(II) complex of claim 3, wherein m is an integer from 1 to 10.

5. A polynuclear α-diimine Ni(II) complex of claim 1, wherein m is 0.

6. A polynuclear α-diimine Ni(II) complex of claim 1, wherein X is Br; m is 0, n is an integer from 1 to 30; $R_1$ is isopropyl, $R_2$ is methyl or isopropyl; $R_3$ and $R_4$ are the same, and are H or methyl, or $R_3$ and $R_4$ form a cyclohexyl group; and $R_5$ and $R_6$ are methyl.

7. A polynuclear α-diimine Ni(II) complex of claim 1, wherein, X is Br; m is 0, n is an integer from 1 to 20; $R_1$ and $R_2$ are isopropyl; $R_3$ and $R_4$ are the same, and are H or methyl; and $R_5$ and $R_6$ are methyl.

8. A polynuclear α-diimine Ni(II) complex of claim 1, wherein, X is Br; m is an integer from 1 to 10, n is an integer from 1 to 20; $R_1$ is isopropyl, $R_2$ is methyl or isopropyl; $R_3$ and $R_4$ are the same, and are H or methyl, or $R_3$ and $R_4$ form a cyclohexyl group; and $R_5$ and $R_6$ are methyl.

9. A polynuclear α-diimine Ni(II) complex of claim 1, wherein X is Br; m is an integer from 1 to 10, n is an integer from 1 to 20; $R_1$ and $R_2$ are methyl; $R_3$ and $R_4$ are the same, and are H or methyl; and $R_5$ and $R_6$ are methyl.

10. A method for the preparation of the polynuclear α-diimine Ni(II) complex of claim 1, comprising the steps of:

(a) condensing an a-diketone represented by the formula I, II or a mixture thereof,

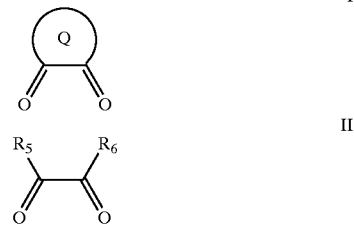

a substituted aromatic diamine represented by the formula

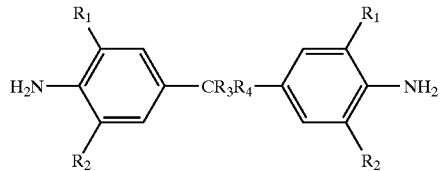

and a substituted aromatic amine represented by the formula

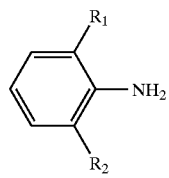

in a medium of alcohol, aromatic hydrocarbon, alcohol-ether mixture, or alcohol-halogenated hydrocarbon mixture and under the catalytic action of HCOOH, $CF_3COOH$, HF, HCl, HBr, or HI; thereby obtaining an oligomer of substituted α-diimine of the formula

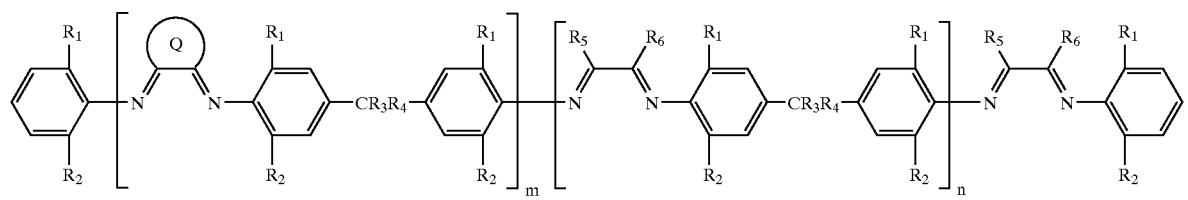

(b) carrying out a coordination reaction of the oligomer of step (a) with $NiX_2$, in the absence of water and oxygen, thereby obtaining a polynuclear α-diimino Ni(II) complex of the following formula:

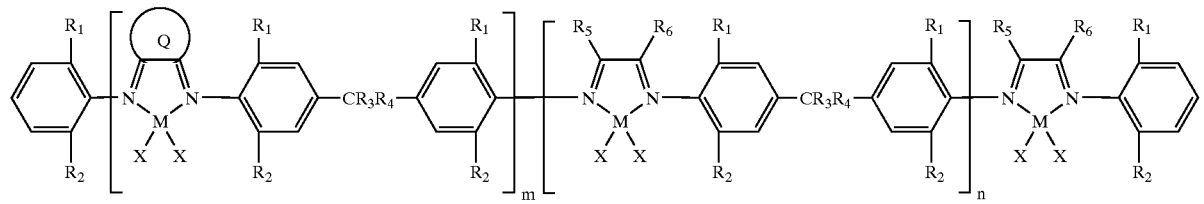

wherein, $R_1$, $R_2$, $R_3$, $R_4$, $R_5$, $R_6$, Q, M, X, m and n are as defined in claim 1.

11. A method for preparing polyethylene, comprising contacting ethylene with the polynuclear α-diimine Ni(II) complex of claim 1 in the presence of a cocatalyst.

* * * * *